United States Patent [19]

Härle

[11] Patent Number: 4,504,266
[45] Date of Patent: Mar. 12, 1985

[54] VARIABLE ASPIRATION DRAINING INSTRUMENT

[75] Inventor: Anton Härle, Schelmenstiege 8, D-4400 Münster, Fed. Rep. of Germany

[73] Assignee: Anton Härle, Münster, Fed. Rep. of Germany

[21] Appl. No.: 475,469

[22] Filed: Mar. 18, 1983

Related U.S. Application Data

[62] Division of Ser. No. 215,687, Dec. 12, 1980, abandoned.

[30] Foreign Application Priority Data

Dec. 14, 1979 [DE] Fed. Rep. of Germany ....... 2950323

[51] Int. Cl.³ .............................................. A61M 1/00
[52] U.S. Cl. ..................................... 604/118; 251/303
[58] Field of Search ........................ 604/118, 119, 902; 15/419, 421, 357, 361; 251/298, 299, 303; 433/95

[56] References Cited

U.S. PATENT DOCUMENTS

| | | | |
|---|---|---|---|
| 173,556 | 2/1876 | Patton | 251/303 |
| 1,403,509 | 1/1922 | Long | 251/322 |
| 2,511,238 | 6/1950 | Beede | 15/419 X |
| 2,539,559 | 1/1951 | Ward et al. | 251/299 |
| 2,574,036 | 11/1951 | Henchert | 251/322 |
| 2,699,318 | 1/1955 | Ellison et al. | 251/298 |
| 2,763,406 | 9/1956 | Countryman | 251/303 |
| 3,148,700 | 9/1964 | Friedell | 251/322 |
| 3,539,150 | 11/1970 | Conrad | 251/298 |
| 3,608,579 | 9/1971 | Moore | 251/298 |
| 3,645,497 | 2/1972 | Nyboer | 128/276 |
| 4,212,300 | 7/1980 | Meals | 128/276 |
| 4,299,221 | 11/1981 | Phillips et al. | 128/276 |

FOREIGN PATENT DOCUMENTS 1166670 10/1969 United Kingdom ............... 128/276

Primary Examiner—C. Fred Rosenbaum
Assistant Examiner—J. L. Kruter
Attorney, Agent, or Firm—Peter K. Kontler

[57] ABSTRACT

An aspiration instrument for the aspiration of liquids in a surgical operation takes the form of an aspiration pipe. This aspiration pipe has a check valve, which may be opened by way of a lever, button or the like and by which the aspiration effect may be shut off when the lever or the like is let go of.

6 Claims, 3 Drawing Figures

VARIABLE ASPIRATION DRAINING INSTRUMENT

This application is a division of application Ser. No. 215,687, filed Dec. 12, 1980, now abandoned.

BACKGROUND OF THE INVENTION

The present invention is with respect to an aspirating or draining instrument, more specially for the aspiration of liquids in surgical operations using an aspiration pipe to be kept by hand in the operation wound.

Such an instrument which, as a general rule, has so far been in the form of a simple aspiration pipe, is joined up with a bottle, for trapping aspirated or drained liquid, and which is, in turn, joined up with the vacuum line of the hospital or other building. The aspiration pipe is placed by hand at a position which is to be kept clear of liquid, and the aspirating effect is kept up all the time even while the pipe is not taking up any liquid. After the operation, the aspiration pipe, its connection hose running to the bottle and any connection pieces and the like together with the bottle itself, are thrown away.

OUTLINE OF THE INVENTION

One purpose of the present invention is that of diminuation the introduction of microorganisms into the wound or site of the operation by use of the aspiration pipe.

For effecting this and other purposes, in the invention an aspirating instrument of the sort noted has a shut off controlling part in it for the vacuum.

The invention is based on the discovery that keeping the aspiration instrument in use at all times, even when no liquid is to be aspirated, has the effect of aspirating not only unnecessary air, but furthermore microorganisms, which are deposited at the inlet end of the aspiration pipe, this end being wetted by contact with the liquid to be aspirated so that the microorganisms from the air will be likely to be kept sticking on it forming a deposit, at the end of the aspiration pipe, which is directly touching the wound. This undesired effect, however, may be stopped with the shut off controlling part for the aspiration vacuum in the present invention.

In the past drain or aspiration pipes have been put forward which, for controlling their aspiration effect, have a hole at some distance from the inlet end of the pipe, which hole may be more or less, as may be desired, covered over by the index finger. In the case of such an aspiration pipe, however, there will still be a small aspiration effect through the distal end when the hole is open, and the building up of deposits of microorganisms at the distal end of the pipe will only be lessened to some degree. Furthermore, microorganisms will be deposited round the finger hole, whose edge may be kept wet to some degree by the finger used for shutting it. Building up microorganism deposits at this position is not unimportant, because such microorganisms may well be taken up by the surgeon's finger, on covering up the hole again, and then such microorganisms may well get into the operation wound from the finger.

On the other hand, in the present invention, the aspiration of air through the pipe is hut off at all, at least with respect to the aspiration pipe which is being manipulated.

In a further development of the invention an effect of great value is produced because the shut off part takes the form of a valve placed in the aspiration pipe so that the valve may be worked by the hand of the user, for example with the index finger. In this form of the invention, the use of the instrument is specially simple, this being more specially important if the valve is not only to be used for complete shut off and complete opening of the lumen of the pipe, but furthermore is to be used for aspiration rate control with an adjustment between the fully shut off and fully opened condition. The valve may be specially designed for such a stepless or other rate control. To a certain degree, however, the controlling effect will be automatic.

As a further development of the invention, the aspiration pipe may be made up of two pipe lengths joined together by way of a housing and the one end of the pipe, which is best cut at a slope, is designed as a seat in the housing for a valve door or flap, there furthermore being a pin running through an elastic part of a wall of the housing so that, using the pin, the valve flap may be lifted clear of its seat, the sloping design being responsible for the useful effect that even on a small angle of turning taking place, the inlet end of the pipe is more or less completely uncovered.

In accordance with a further development of the invention of good effect, the valve is made, more specially by injection molding, of synthetic resin, with two female holes in which the ends of the two-piece aspiration pipe are placed so that the valve is between them, and in the body, more specially generally in line with the one pipe end, there is a valve seat with a valve shutting part, which is fixed on a rod running slippingly through the wall of the synthetic resin body and having a grip on its outside end. Such a valve is low in price and trouble-free in operation.

Furthermore, it is to be best for the end, supporting the valve shutting part, of the rod to be designed running through the valve seat while the other end, running out through the synthetic resin body, is acted upon by the pulling force of a spring, the handle or grip then only being in the form of a button. With this design there is no change in the direction of motion of the parts, that is to say they are all moved along a straight line. Furthermore, the design is specially low in price and trouble-free in operation.

The spring may best be made in the form of a coil or helical spring placed round the rod and let, at least in part, into a hollow in the synthetic resin body, the other end of the spring simply resting against the grip or button.

DETAILED ACCOUNT OF WORKING EXAMPLES OF THE INVENTION

Working examples of the invention will be seen in the accompanying figures.

Figures 1, 2, 3:
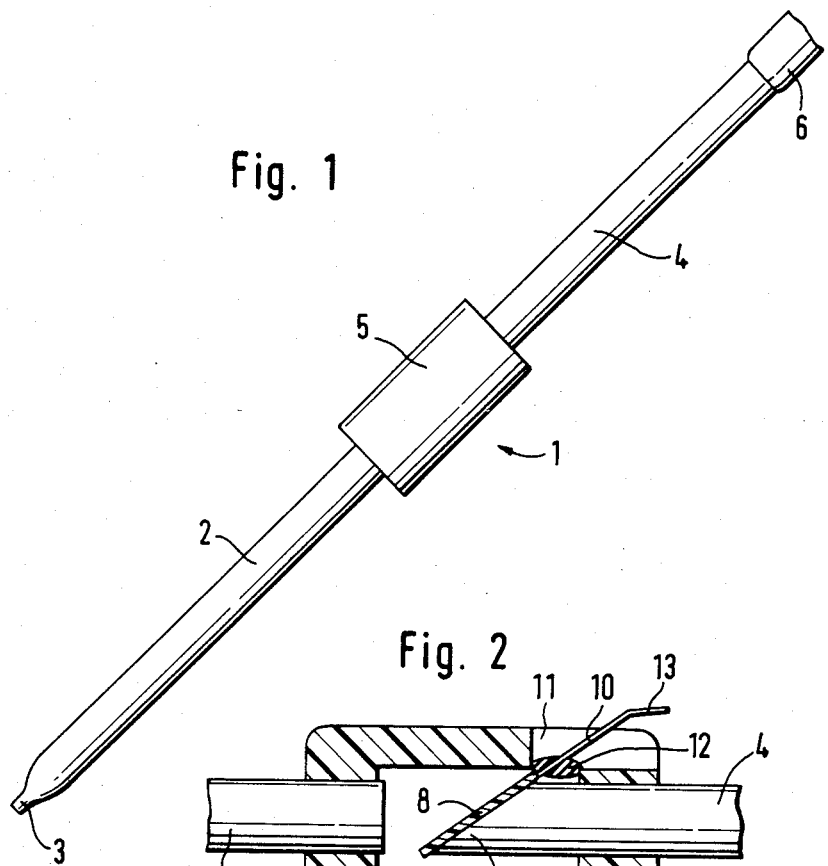
FIG. 1 is a general side view of an aspiration pipe with a valve.
FIG. 2 is a view, on a greater scale, of the valve in lengthways section.
FIG. 3 is a lengthways section of an other form of the valve.

Turning now more specially to FIG. 1, it will be seen that an aspiration drain or instrument 1 is made up of a distal pipe length 2, which distally becomes narrower to take the form of a flat inlet end 3. There is furthermore a proximal pipe length 4 and between these lengths a valve 5 is placed. The proximal end of pipe length 4 is joined up with an aspiration hose 6 or flexible pipe.

For forming the valve 5, in the design of FIG. 2, the proximal pipe length 4 is cut to take the form of a slopingly placed end 7, which may be shut off by a door or flap 8. Flap 8 is turningly supported on a pin 10 in the housing 9 joining the two lengths 2 and 4 of the instrument together. Pin 10 may be pointed and simply pushed into flap 8, on putting the parts together, like a needle, the pin running out of housing 9 through a cutout 11 (stretching in the length-direction) for the flap and being supported by a stopper or mass 12 of a highly elastic sealing material (between the cutout and the inner space of housing 9). The outer end of pin 10 is bent somewhat for forming a finger rest 13, in the direction of pipe length 4.

On use the index finger of the hand supporting the instrument 1 is placed on rest 13 and pin 10 is turned, the sealing stopper 12 acting as a bearing because of its elastic properties. For this reason, flap 8 is moved clear of sloping pipe end 7 freeing the way for air to be aspirated through the instrument. On letting go of finger rest 13, the flap or door 8 will be pulled by the aspirated air and so shutting off the end of pipe length 7 with the effect of a check valve.

In the form of the invention of FIG. 3, valve 5 is made up of an injection-molded body 14 with a seat ring 15 for a bell-like valve stopper. Pipe lengths 2 and 4 are out of line in the axial direction and run into opposite ends of body 14. Past the end of the proximal or back pipe length 4 there is a rod 17, supporting valve stopper 16, which is taken up by a hole 18 in the wall of body 14 so that it may be moved in the length-direction and at its outer end has a pushbutton 19 fixed on it. The outer end of the hole 20 in which rod 17 is slippingly supported is made somewhat greater in diameter for housing a coil or helical spring 21 with the function of pushing button 19 outwards so that valve stopper 16 is forced against its seat ring 15.

On using the aspiration pipe 1, the valve is pushed open by the index finger of the hand in which the pipe or instrument is being supported so that, on pushing against button 19, the valve is opened.

All the parts of the system but for the pin 10 and spring 21 are made up of plastics material and are joined together by putting a solvent on the ends of pipe lengths 2 and 4 (for example) and then pushing them into the housing.

I claim:

1. An aspirator for use during a surgical procedure to remove flowable material from a surgical wound, said aspirator comprising a tubular body having a first end and a second end and a passage between said ends, said first end having a first opening for connecting said passage with a source of suction and said second end having a second opening for the withdrawal of flowable material from the wound, said passage communicating with the exterior of said body only via said openings; a tubular member extending through said first opening and having a sloping end face disposed in said passage; and regulating means on said body for regulating the suction in said passage when the latter is connected to a source of suction, said regulating means including a valve member movable between an open position in which said valve member is remote from said sloping end face and in which said second opening communicates with said first opening, and a closed position in which said valve member sealingly engages said sloping end face and such communication is interrupted, and said regulating means further including a manually operated actuating member for moving said valve member from said closed position to said open position, said valve member being biased toward said closed position and capable of moving from said open position to said closed position substantially under the action of aspirated air in said passage when said actuating member is released.

2. An aspirator as defined in claim 1, wherein said sloping end face of said tubular member defines a seat and said vale member engages said seat in said closed position.

3. An aspirator as defined in claim 1, further comprising a resilient sealing member in said body, said valve member comprising a flap and said actuating member comprising a pin which is supported by said sealing member.

4. An aspirator as defined in claim 1, wherein said regulating means is located internally of said body.

5. An aspirator as defined in claim 1, wherein said body is designed to be hand-held by a member of a surgical team and said is operable by a hand which holds said body.

6. An aspirator as defined in claim 5, wherein said is operable by the index finger of a hand which holds said body.

* * * * *